Figure 1:
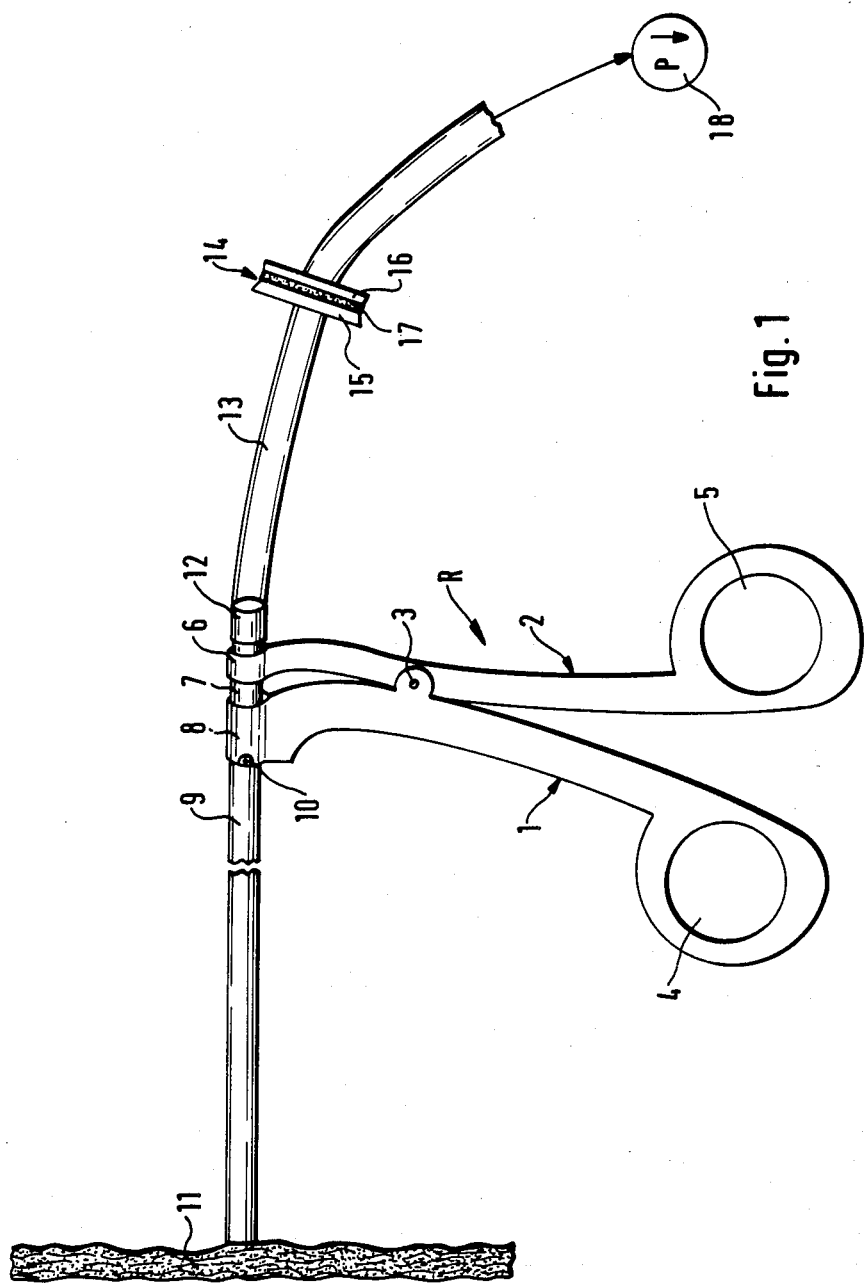

United States Patent [19]

Kothe

[11] Patent Number: 4,881,550

[45] Date of Patent: Nov. 21, 1989

[54] MEDICAL INSTRUMENT

[76] Inventor: Lutz Kothe, Bodmaner Str. 17, D-7760 Radolfzell 14, Fed. Rep. of Germany

[21] Appl. No.: 155,917

[22] Filed: Feb. 16, 1988

[30] Foreign Application Priority Data

Feb. 18, 1987 [DE] Fed. Rep. of Germany ... 8702446[U]

[51] Int. Cl.$^4$ ............................................. A61B 17/32
[52] U.S. Cl. ..................................... 128/752; 604/22; 128/751; 128/305
[58] Field of Search ............... 128/305, 321, 751, 752, 128/312, 303 A, 345, 356; 604/22; 294/99.2; 30/187-190, 264

[56] References Cited

U.S. PATENT DOCUMENTS

| | | | |
|---|---|---|---|
| 1,274,669 | 7/1918 | Bohn | 128/312 |
| 3,964,468 | 6/1976 | Schulz | 128/305 |
| 4,246,902 | 1/1981 | Martinez | 128/305 |
| 4,427,014 | 1/1984 | Bei et al. | 128/305 |
| 4,522,206 | 6/1985 | Whipple et al. | 604/22 |
| 4,662,371 | 5/1987 | Whipple et al. | 128/305 |

FOREIGN PATENT DOCUMENTS 2479680 12/1982 France ............................. 128/305
0066465 6/1981 United Kingdom ............... 128/321

Primary Examiner—Michael H. Thaler
Assistant Examiner—William Lewis
Attorney, Agent, or Firm—Bachman & LaPointe

[57] ABSTRACT

In a medical instrument are provided cutting forceps for taking tissue samples, removing elongated body elements, such as nerve or vein portions, or the like. An inner tube (7) is inserted in an outer tube (9). One tube (7 or 9) is axially displaceable against the other tube (9 or 7). One of the tubes (7 or 9) has the cutting forceps (20), whose closing movement is dependent on the other tube (9 or 7), the cutting forceps (20) comprising two cutting blades (21, 22), which have cutting edges (23) and common pivots (25) with a tube (7 or 9). The in each case other tube (7 or 9) has depressions (26) in the terminal edge (27), in which the pivots (25) are inserted during the closing of cutting forceps (20). The contours of depressions (26) are adapted to the outer contours of the cutting blades (21, 22).

21 Claims, 5 Drawing Sheets

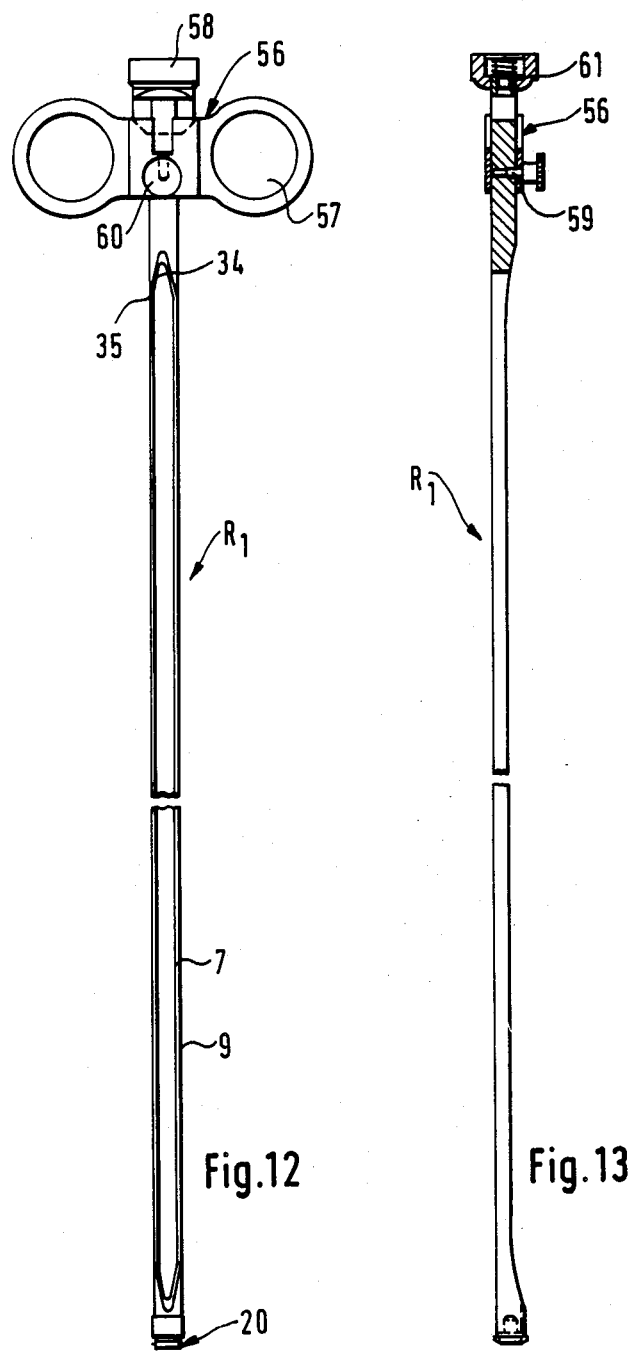

MEDICAL INSTRUMENT

The invention relates to a medical instrument with cutting forceps for taking tissue samples, removing elongated body elements, such as nerve or vein portions, etc., an inner tube being inserted in an outer tube and one tube is axially displaceable against the other and in which one tube has the cutting forceps, whose closing movement is dependent on the other tube, the cutting forceps comprising two cutting blades, which have cutting edges and common pivots with one tube.

On taking tissue samples use is made of so-called sample or exploratory excision forceps, which are introduced into the human body, pinch or cut off a tissue sample and hold the same on removing the forceps. The tissue sample is then placed on a corresponding substrate.

If several tissue samples are to be taken, this means that for each individual sample, the excision forceps must again be introduced into the human body and as a result of tissue displacement it is often difficult to find the desired point again from which as yet no sample has been taken.

Moreover, in the known exploratory excision forceps, the cutting movement of the cutting forceps is generally brought about by an inner rod guided in the bore of a tube, which makes it possible to remove the cut off sample through said bore.

For the last-mentioned reason such instruments are only suitable for taking tissue samples. For example, if they are used for removing elongated body elements, such as nerve or vein portions, then operating incisions must be made in spaced manner on the corresponding body parts and in this way the body element to be removed is cut off piece by piece.

European patent application No. 0 119 405 e.g. discloses a surgical instrument, in which two tubes are displaceably guided within one another, the inner tube performing the closing movement of a cutting blade. This instrument has the disadvantage that its opening width is very limited. Moreover, its closing movement, i.e. also the cutting action is solely dependent on the pressure under which the inner tube is guided. For taking tissue samples from e.g. smooth tissue walls which the instrument meets at right angles, it is not possible to use said instrument.

FR-A-No. 2 479 680 discloses forceps, in which two forceps jaws are spread apart by the pressure of an inner tube and are closed by tension. Here again, there is much to be desired in connection with the force transfer. This instrument does not make it possible to cut off tissue samples or remove elongated body elements.

The problem of the invention is to develop an instrument of the aforementioned type making it possible to take a plurality of tissue samples, without having to remove the instrument from the human body. Moreover, this instrument is not only intended for use for taking tissue samples, but also for other operative measures, such as e.g. the removal of elongated body elements, such as nerve or vein portions. In addition, the force transfer to the cutting forceps is to be considerably improved, so that a smooth cutting off occurs instead of a pinching of e.g. the tissue samples or elongated body elements.

This problem is solved in that in each case other tube has depressions in the terminal edge and the pivots are introduced into the same on closing the cutting forceps.

In the case of such an instrument no cable line is now required for the closing movement of the cutting forceps, so that the core of the inner tube can be used for taking tissue samples. For reasons of simplicity, the samples are taken by means of a vacuum, as will be described hereinafter.

Suitable cutting forceps are constituted by two cutting blades, which have cutting edges and a common pivot with the tube. The cutting blades can either be externally fixed to the inner tube or internally fixed to the outer tube, preference being given to fixture to the inner tube.

The in each case other tube, which carries no cutting forceps, has depressions in the terminal or end edge and the pivots can be introduced into the same on closing the cutting forceps. The depression edges firstly meet the cutting blades, raise the same and surround them in the closed position. For this purpose the contours of the depressions are adapted to the outer contours of the cutting blades. This is preferred, but is not prescribed.

A reliable closing of the cutting blades can be attributed to this extremely simple measure and the cut off tissue sample is immediately removed by suction. There is no need to remove the instrument from the human body and further samples can instead be cut by it in the vicinity of the tissue sample which has just been taken.

In practice, difficulties can occur because the cutting blades do not automatically open after cutting off a tissue sample. This problem can be obviated by corresponding spring elements, but this involves considerable constructional expenditure. Therefore, for reasons of simplicity, a bolt engaged with the cutting blades is provided and on returning the tube causing the cutting movement carries with it and opens the cutting blades. Preference is given to a guide recess in the cutting blade and which serves as a link for the bolt. However, this is not intended to limit the inventive concept.

According to another embodiment of the invention the cutting blades are connected by means of fastening plates to the tube. These fastening plates have a hook by means of which they engage in a corresponding recess in the cutting blades, whilst the other end thereof is connected by means of bolt portions or the like to the tube. These bolt portions are then welded into the tube for reasons of simplicity. The fastening plates have in particular the function of opening the cutting device. Here again, closure takes place by means of corresponding depressions shaped into the terminal edge of the tube.

According to a simple embodiment of the invention, the cutting blades have engagement troughs, in which engage corresponding detents or latches of the tube. On opening and closing, these detents virtually roll in the engagement troughs and a corresponding engagement trough is formed in the tube and in the later once again engage corresponding detents from the cutting blades, so that in this way a roller bearing is formed.

If the inventive instrument is to be used not only for taking tissue samples, but e.g. also for removing elongated body elements, it is obvious that no vacuum connection is required. In this case, both the outer and the inner tube has a notch, which permits access to the inner tube core. In this way it is e.g. possible to introduce a nerve tract into the opening of the inner tube and pass out to the notches. The surgeon can hold the nerve end, whilst moving the instrument further over the nerve tract and cutting same off at a remote end. It may also be necessary for the aforementioned purpose to make both the outer and inner tube from flexible material.

In this simple embodiment of the inventive instrument, for actuating purposes it is sufficient for the inner tube to be firmly connected to a handle, whilst the outer tube is also supported against an axially movable screw head. When pressure is exerted on the screw head, the outer tube is axially displaced and closes the cutting forceps. For opening purposes, there is an axial displacement of the outer tube by retracting the screw head.

In some cases it can be advantageous if in this case the screw head engages with a threaded portion in the inner tube, so that its force is transferred to the outer tube by screwing. As soon as a particular stop is reached, the surgeon knows that the cutting forceps are closed. The screwing movement can also improve the force transfer. It is advantageous in this case if the outer tube is guided which, for reasons of simplicity, takes place by a pin in the handle, which traverses a slot in the outer tube.

This can also prove advantageous in the case of use as removal forceps and e.g. when removing gall-stones or the like. Small stones can be shattered by the cutting forceps and the fragments can be sucked through the inner tube core. This also applies if the stones are shattered by known means prior to the removal of the fragments.

In the preferred embodiment, in which the inner tube carries the cutting forceps and the outer tube is used for closing the latter, the outer tube is connected by means of joint plates to a sleeve shaped on to the forceps arms, said sleeve surrounding the inner tube in clearance-free manner. This ensures the corresponding necessary mobility of the connection. In addition, the inner tube traverses a sleeve shaped on to the other arm and is provided with a connecting nipple, on which can be mounted a line leading to a vacuum pump.

In another actuator embodiment, the outer tube is firmly connected to a casing which houses a valve means forming or interrupting a connection between an axial bore in the inner tube and the line to the vacuum pump. In practice, it has proved advisable for the medical instrument not be under vacuum for the entire working period. If e.g. the instrument is moved in the human body, it may be necessary over a considerable distance for it not to suck up extraneous material.

Thus, with respect to this valve means, the inner tube can be connected to an insert, which engages with a tube portion in the connecting nipple. This insert is displaceably mounted in a casing trough. In said insert is rotatably located a rotary head, which has a transverse bore for connecting the axial bore and line. This rotary head engages with a hinge pin in the casing and is also shaped on one forceps arm, which traverses a corresponding recess in the casing. If this forceps arm is moved, then it displaces the insert and simultaneously the rotary head is rotated relative to the insert and the transverse bore passes out of axial alignment with the axial bore and the line, so that the valve is closed.

A collecting device is provided in the line for collecting tissue sample and has at least one collecting fabric. However, more complicated devices are conceivable and the collecting device is constructed in such a way that it automatically opens after collecting a tissue sample and the next collecting fabric is inserted.

The vacuum connection has a further important advantage when removing tissue samples. When placing the head region of the instrument on the tissue, the latter is partly sucked into the opening of the inner tube, so that a larger tissue sample can be taken. Particularly when taking tissue samples from smooth surfaces, this has proved to be particularly effective. Moreover, the cutting blades are so arranged that there is lead cutting, i.e. they always engage over the inner tube opening.

The new tumour and sample excision forceps are particularly intended for the following functions:

biopsy of solid tissues, tumours, lymph nodes and the walls of hollow organs;

endoscopic removal of surface changes such as polyps, tumours, granulomas, etc.;

endoscopic biopsy of surface changes such as ulcers, inflammations, aggregate follicles and other mucous membrane changes;

removal of free arthrophytes and degenerative materials from large joints.

The inventive instrument is intended for use in gynaecology, for endoscopic treatment of the vagina, ectocervix and uterus, gastroenterology in the endoscopy of the lower colon sections, pulmonology in mediatinoscopy and rigid bronchoscopy, as well as minithoractomy, ENT medicine in laryngoscopy and endoscopy of the nasal sinuses, urology in cystoscopy and possibly prostatic surgery and orthopedic surgery in the arthroscopy of large joints.

In a technical further development to a flexible instrument, it would be possible to use it in connection with esophagogastroduodenoscopy, coloscopy, deep bronchoscopy and arthroscopy of central joints.

The present invention leads to the following advantages.

As a result of pinch-free incision, the tissue samples are protected and histological evaluation is made easier and more reliable.

The special cutting mechanism makes it possible to take samples without the instrument having to be pressed against the tissue, as is the case with conventional forceps. This leads to a clearly defined depth of cut and to a clearly defined removed tissue volume. The risk of perforation is minimized and the number of removal actions is reduced as a result of the adequately large tissue portion.

The direct suction removal of the tissue parts makes it possible for the surgeon to permanently keep an eye on the biposy point using the optics. The instrument and optics can be constantly directed on the area of interest, whereas when taking samples up to now, the tissue had to be removed with the forceps. This involves a constant introduction and removal of the forceps. It is now no longer necessary for the investigative area to be sought several times with the biopsy forceps.

It leads to a speedier, more rational and more patient-friendly investigative procedure. It also makes it possible to remove larger tissue portions, such as broad-based tumours.

The safety of bioptic investigations is increased and for the patient this can lead to a stricter indication position for more invasive treatments, such as operations.

Complications during biopsy, such as e.g. afterbleeding and the like can be rapidly detected and dealt with, because the surgeon's eye is always directed on the sample removal point.

The biopsy forceps also permit a suction of liquids. This leads to good viewing conditions during endoscopy, e.g. through the sucking off of blood or secretion, without any operating instrument change being necessary.

The biopsy forceps itself makes it possible to remove liquids for diagnostic purposes, such as e.g. for irrigating cytology.

Further advantages, features and details of the invention can be gathered from the following description of preferred embodiments with reference to the drawings, wherein show:

FIG. 1 A part sectional, perspective representation of an inventive sample excision forceps in the use position.

Figure 2:
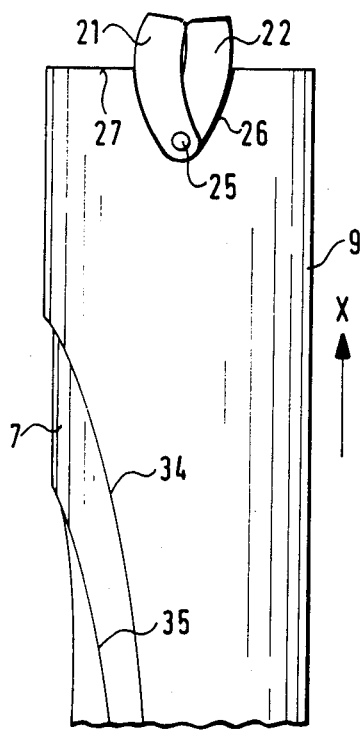

FIG. 2 A plan view of an embodiment shown on a larger scale of the cutting area of forceps according to FIG. 1 in the closed position.

Figure 3:
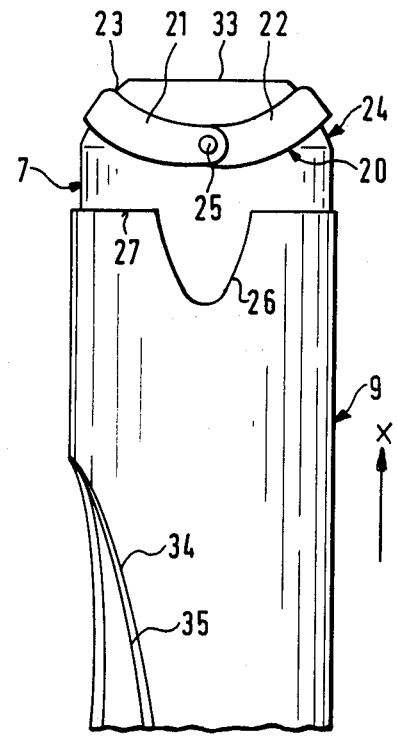

FIG. 3 A plan view of the embodiment according to FIG. 2 in the open position.

Figure 4:
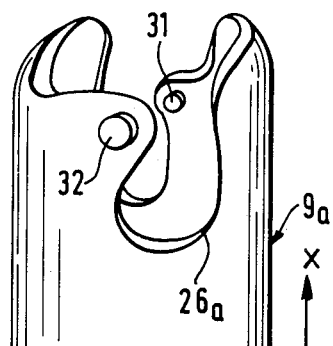

FIG. 4 A perspective view of an outer tube of a further embodiment of the inventive forceps.

Figure 5:
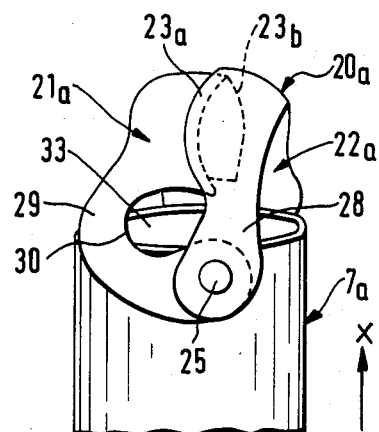

FIG. 5 A perspective plan view of the inner tube of FIG. 4 with cutting elements.

Figure 6:
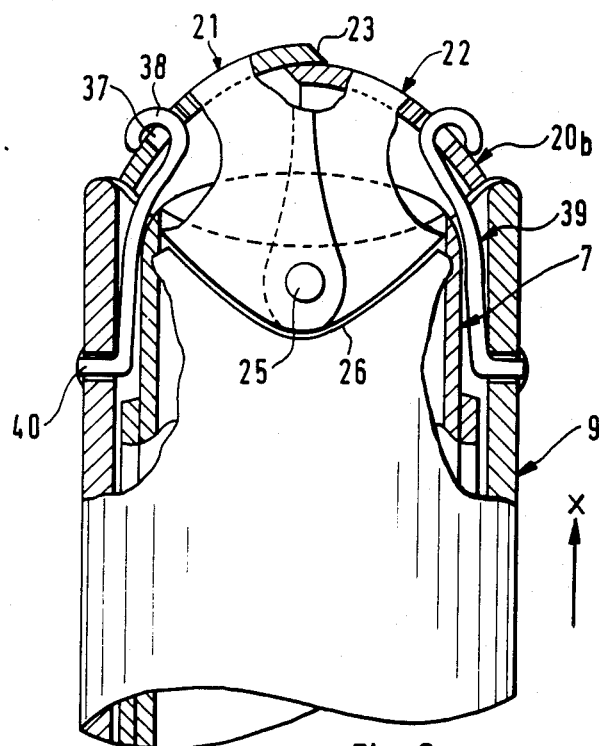

FIG. 6 A perspective and partly broken away view of another embodiment of a cutting area of inventive forceps.

Figure 7:
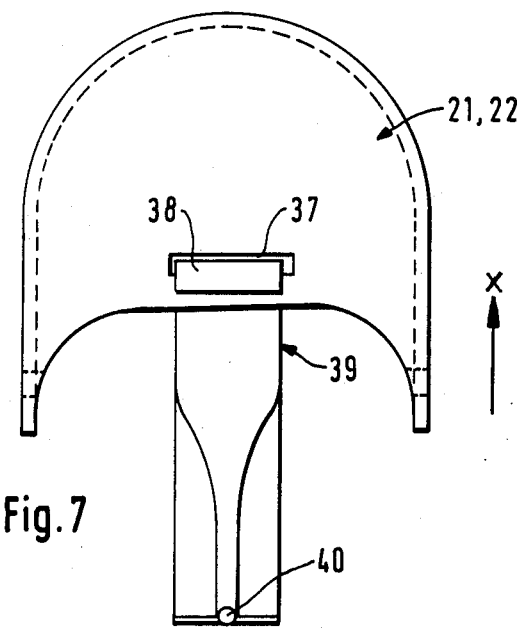

FIG. 7 A plan view of a cutting blade used in the embodiment according to FIG. 6.

Figure 8:
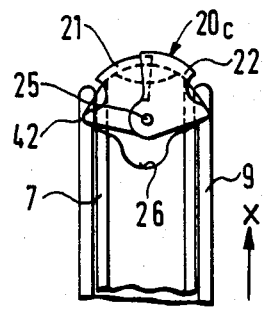

FIG. 8 A perspective view of another embodiment of a cutting area in the closed position.

Figure 9:
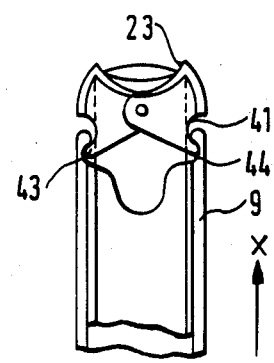

FIG. 9 A perspective view of the cutting area according to FIG. 8 in the open position.

Figure 10:
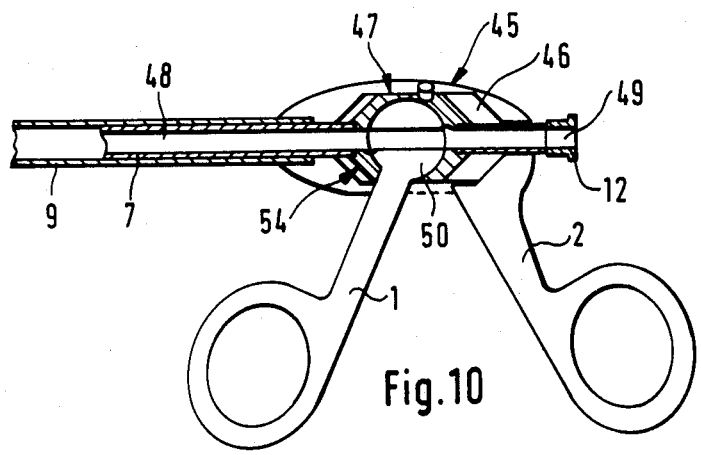

FIG. 10 A longitudinal section through another embodiment of an exploratory or sample excision forceps in the vicinity of the handle with the valve open.

Figure 11:
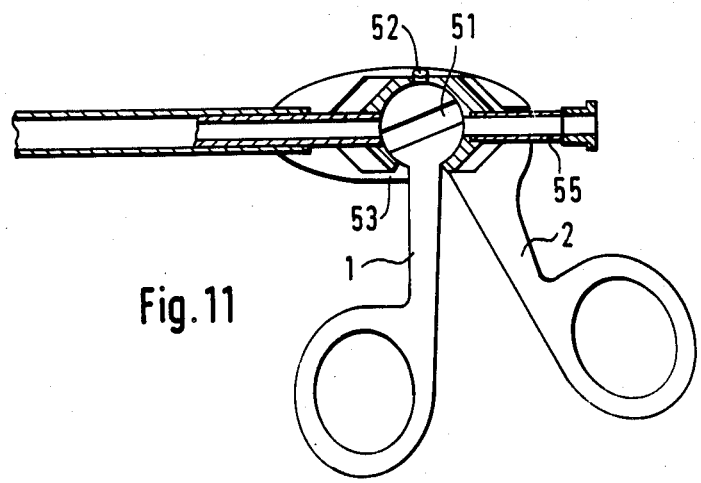

FIG. 11 The longitudinal section according to FIG. 10 with the valve closed.

FIG. 12 A plan view of another embodiment of a sample excision forceps.

FIG. 13 A part secional side view of the forceps of FIG. 12.

An exploratory or sample excision forceps R has, according to FIG. 1, two forceps arms 1 and 2, which are interconnected by means of a joint 3. On one side each forceps arm 1 or 2 has a gripping opening 4 or 5, in which is inserted the finger of a human hand. On the other side of the joint a sleeve 6 is shaped on to the forceps arm 2 and in it is inserted an inner tube 7. Forceps arm 1 also has a sleeve 8 on the other side of the joint and surrounds the inner tube 7 in clearance-free manner and is connected to an outer tube 9 by means of joint plates 10. Outer tube 9 surrounds inner tube 7 and in the use position passes together therewith onto a tissue portion 11 in the human body.

Inner tube 7 passes through sleeve 6 on the other side of sleeve 8 and forms a connecting nipple 12 for a hose 13. In the latter is provided a collecting device for tissue samples, which e.g. comprises two interconnected perforated disks 15, 16, between which is placed a collecting fabric 17. Following said collecting device 14, hose 13 leads to a diagrammatically indicated vacuum pump 18.

FIGS. 2 to 9 show different embodiments of cutting areas of the sample excision forceps, which in the use position meet the tissue portion 11 according to FIG. 1. According to the invention, in the head region is provided a cutting forceps 20 comprising two cutting blades 21, 22. Each cutting blade has a cutting edge 23. In the open position, both cutting blades 21, 22 surround the rounded head region 24 of inner tube 7 and have common, facing pivots 25 by means of which they are also fixed on the inner tube 7. Outer tube 9 has in its apex region a depression 26, whose inner contour roughly corresponds to the outer contour of cutting blades 21, 22.

For closing the forceps, inner tube 9 is moved in direction x according to FIG. 2 and its terminal edge 27 meets the cutting blades 21, 22, which are drawn up and pivot 25 passes into depression 26. In the closed position, the two cutting edges 23 of cutting blades 21, 22 meet one another and in this way can cut off a tissue sample. This tissue sample is sucked away by the vacuum applied to inner tube 7 and is collected in collecting fabric 17.

For the non-rotary mounting of inner tube 7 with respect to outer tube 9, the two tubes can have corresponding, not shown centring grooves or projections.

FIGS. 4 and 5 show a further embodiment of cutting forceps 20a. Here again, the cutting forceps 20a comprises two cutting blades 21a, 22a, which form a common pivot 25 with the inner tube 7a. In the case of cutting forceps 20a, the cutting blades 21a, 22a are so constructed that the cutting edge 23a of one cutting blade 22a overlaps the cutting edge 23b (shown in dotted line form) of the other cutting blade 21a. Each cutting blade 21a or 22a has on the one side a tongue 28 towards one pivot 25 and towards the other pivot 25 a rocking arm 29, which forms a guide recess 30. If inner tube 7a is inserted in outer tube 9a according to FIG. 4, then bolts 31 engage in the particular guide recess 30. The bolt 31 can be e.g. turned in the material of outer tube 9a, so that only bolt head 32 is visible from the outside.

For closing the cutting forceps 20a, tongue 28 of cutting blade 22a moves into depression 26a and cutting blade 22a is drawn up. On the other side, the tongue of cutting blade 21a passes into its associated depression, so that blade 21a is also drawn up. However, if outer tube 9a is retracted counter to diraction x, then the bolts 31 in guide recess 30 again take the cutting blades 21a or 22a with them and open the cutting forceps 20a.

In the case of cutting forceps 20b according to FIGS. 6 and 7, an inner tube 7 is again inserted in an outer tube 9. Once again the two cutting blades 21, 22 have the common pivot 25 on inner tube 7. The cutting edges 23 overlap in this embodiment.

Each cutting blade 21 or 22 has a recess 37 as is particularly clearly visible in FIG. 7. In said recess 37 engages a hook 38 of a fastening plate 39. To the other end of hook 38, the fastening plate 39 is fixed to outer tube 9, being located in the latter with a corresponding bolt portion 40. Bolt portion 40 can e.g. be welded to outer tube 9.

It is also possible to clearly see the depression 26 in outer tube 9, which leads to the correct closure of cutting blades 21, 22. If outer tube 9 is moved in direction x, then it is also followed by the fastening plates 39, which take the cutting blade 21, 22 with them. These cutting blades 21, 22 move into depression 26, so that closure is brought about and the cutting edges 23 overlap. Thus, e.g. a tissue portion is cut off and can be further conveyed in the inner tube.

If the outer tube is moved counter to direction x, then the fastening plates 39 carry the cutting blades 21, 22 with them, so that the latter rotate about pivot 25 and open.

Another, very simple embodiment of cutting forceps 20c is shown in FIGS. 8 and 9. Here again, outer tube 9 surrounds inner tube 7 and the opening and closing movement of the cutting forceps 20c is brought about by the outer tube 9. Cutting blades 21, 22 once again rotate about pivot 25, which fixes same to inner tube 7.

However, according to the invention, each cutting blade 21 or 22 has an engagement trough 41, in which engages a correspondingly shaped latch or detent 42 of outer tube 9. Each cutting blade 21 or 22, beside the engagement trough 41, has a corresponding detent 43, which in turn engages in the engagement trough 44 in outer tube 9. As a result of this interaction of engagement trough 41 and detent 42, as well as detent 43 and engagement trough 44, cutting forceps 20c are opened and closed on reciprocating outer tube 9.

FIGS. 10 and 11 show another embodiment of the actuator for a sample excision forceps. The displacement of inner tube 7 with respect to outer tube 9 takes place by means of forceps arm 1. Outer tube 9 is fixed in a casing 45, which is shaped on to the other forceps arm 2 and has a trough 46 for receiving a valve means 47. The latter makes it possible to produce a connection between an axial bore 48 in inner tube 7 and the connecting nipple 12 or its inner bore 49. As indicated, by means of the connecting nipple 12 the tissue sample is sucked through the suction opening 33 and axial bore 48.

For the opening and closing of valve means 47, the forceps arm 1 has a rotary head 50 with a transverse groove or bore 51. Arm 1 is mounted by means of a hinge pin 52 in casing 45. On the other side of said hinge pin 52, the forceps arm 1 passes through a corresponding longitudinal opening 53 in casing 45.

Rotary head 50 is mounted in rotary manner in an insert 54, which can slide in depression 46 during the movement of the forceps arm 1. Insert 54 is on the one hand connected to inner tube 7 and on the other hand to a tube portion 55, which once again slides in the inner bore 49 of connecting nipple 12.

In the open position of the valve means 47 shown in FIG. 10, the transverse bore 51 connects the axial bore 48 to inner bore 49. Cutting forceps 20 are open, so that tissue can be sucked into the suction opening 33.

If the forceps arm 1 is now moved towards the forceps arm 2, then inner tube 7 slides in outer tube 9 and the cutting blades 21, 22 are closed, because they slide into the corresponding depression 26 of forceps 20. Simultaneously the valve means 47 is moved into the closed position shown in FIG. 11, so that it can no longer suck tissue samples. Following cutting off, the valve means 47 can be opened again and tissue sample can again be sucked up. If e.g. the forceps or the cutting forceps 20 are moved into a different point in the human body, then forceps 20 are closed, so that the valve means 47 are interrupted, which prevents permanent suction of undesired fragments.

The inventive exploratory or sample excision forceps are not only intended for taking tissue samples and can instead also be used for removing part of a nerve tract, a vein portion or some similar elongated body element. For this purpose, e.g. the nerve tract is introduced into the suction opening of inner tube opening 7 or 7a and then the latter and outer tube 9 or 9a are moved over and along the nerve tract. However, in order to be able to firmly hold the nerve after insertion, both in inner tube 7 or 7a and in outer tube 9 or 9a is provided a notch 34 or 35. These notches 34, 35 ensure access to the interior of inner tube 7 or 7a.

FIGS. 12 and 13 show a simplified embodiment of forceps R1. Outer tube 9 slides over and beyond the inner tube 7 and actuates the cutting forceps 20, as described in several embodiments hereinbefore. It is also possible to see the corresponding notches 34, 35.

A handle 56 with two gripping rings 57 is located at the upper end. Inner tube 7 is fixed to this handle 56, whilst outer tube 9 can be actuated by pressure on a screw head 58. Outer tube 9 is guided on a pin 59, which passes through a slot 60 in outer tube 9.

Screw head 58 engages with a thread 61 in a corresponding bore in inner tube 7, so that the screw can also lead to a displacement of outer tube 9. If the screw head 58 strikes a not shown stop, this means that the cutting blades 21, 22 of cutting forceps 20 are closed.

I claim:

1. A medical instrument with cutting forceps for taking tissue samples and removing elongated body elements, such as nerve or vein portions or the like, which comprises: an outer tube; an inner tube inserted in said outer tube, with one of said tubes being axially displaceable relative to the other and with one of said tubes having a terminal edge with depressions; cutting forceps affixed to the other of said tubes, said cutting forceps having two cutting blades with cutting edges and common pivots affixed to the other of said tubes, wherein the closing movement of said forceps is caused by the depression acting upon said cutting forceps when said tubes are axially moved relative to each other, and wherein said pivots are introduced into said depressions on closing the cutting edges.

2. An instrument according to claim 1 wherein the depression has a contour and the cutting blades have an outer contour, with the contour of the depression adapted to the outer contour of the cutting blades.

3. An instrument according to claim 1 wherein one of said cutting blades has a tongue which is introduced into said depression, wherein said pivot is associated with said tongue, and wherein the other of said tubes is provided with a bolt, and wherein the other cutting blade is formed by a rocking arm forming a guide recess which engages said bolt.

4. An instrument according to claim 1 wherein the cutting blades are connected by means of fastening plates to one of said tubes.

5. An instrument according to claim 4 wherein the cutting blades have recesses and the fastening plates have a hook with which they engage in the recesses of the cutting blades, and wherein said fastening plates are connected to one of said tubes.

6. An instrument according to claim 1 wherein the outer tube has detents and engagement troughs and wherein the cutting blades have detents and engagement troughs, wherein the engagement troughs of the cutting blades engage the detents of the outer tube and the detents on the outer tube engage the cutting troughs of the cutting blades.

7. An instrument according to claim 1 wherein both the outer tube and the inner tube have a notch in their circumferential surface.

8. An instrument according to claim 1 wherein the inner tube is fixed to a handle and the outer tube is supported against an axially movable screw head.

9. An instrument according to claim 8 wherein the screw head engages with a threaded portion in the inner tube.

10. An instrument according to claim 9 wherein the outer tube is guided over a slot which is traversed by a pin which is fixed to said handle.

11. An instrument according to claim 1 wherein the outer and inner tubes are made from flexible material.

12. An instrument according to claim 1 including a first forceps arm having a sleeve wherein the outer tube is connected by means of joint plates to said sleeve and wherein the sleeve is shaped on said first forceps arm and surrounds the inner tube in a clearance-free manner.

13. An instrument according to claim 12 including a line adjacent said inner tube and a second forceps arm having a sleeve, wherein the inner tube traverses said second forceps arm sleeve and is provided with a connecting nipple for said line.

14. An instrument according to claim 13 wherein the inner tube has an axial bore and wherein the outer tube is fixed to a casing which houses a valve means which produces a connection between the inner tube axial bore and said line.

15. An instrument according to claim 14 wherein the inner tube is connected to an insert which engages with a tube portion in the connecting nipple.

16. An instrument according to claim 15 wherein the insert is displaceably mounted in a trough of said casing.

17. An instrument according to claim 16 wherein a rotary head is rotatably located in said insert and has a transverse bore for connecting the inner tube axial bore and said line.

18. An instrument according to claim 17 wherein the rotary head engages with a hinge pin in the casing.

19. An instrument according to claim 18 wherein said first forceps arm is shaped on the rotary head and traverses a corresponding recess in the casing.

20. An instrument according to claim 13 wherein said line is connected to a vacuum pump.

21. An instrument according to claim 20 wherein upstream of the vacuum pump said line has a connecting device for removed tissue samples.

* * * * *